(12) United States Patent
Jorquera Nieto et al.

(10) Patent No.: US 8,088,416 B2
(45) Date of Patent: Jan. 3, 2012

(54) PROCESS FOR OBTAINING HIGH EFFICIENCY HUMAN ALBUMIN FOR USE IN DETOXIFICATION THERAPY

(75) Inventors: Juan Ignacio Jorquera Nieto, Barcelona (ES); Pere Ristol Debart, Sabadell (ES); Montserrat Costa Rierola, Mataro (ES)

(73) Assignee: Grifols, S.A., Barcelona (ES)

( * ) Notice: Subject to any disclaimer, the term of this patent is extended or adjusted under 35 U.S.C. 154(b) by 428 days.

(21) Appl. No.: 12/268,590

(22) Filed: Nov. 11, 2008

(65) Prior Publication Data

US 2009/0181102 A1    Jul. 16, 2009

(30) Foreign Application Priority Data

Nov. 12, 2007 (ES) .................................. 200702983

(51) Int. Cl.
*A61K 35/14* (2006.01)
(52) U.S. Cl. ....................................................... 424/529
(58) Field of Classification Search .................... None
See application file for complete search history.

(56) References Cited

U.S. PATENT DOCUMENTS

| | | | | |
|---|---|---|---|---|
| 4,440,679 A * | 4/1984 | Fernandes et al. | ............ | 530/363 |
| 5,919,907 A | 7/1999 | Shanbrom | | |
| 6,096,872 A * | 8/2000 | Van Holten et al. | ....... | 530/390.1 |

FOREIGN PATENT DOCUMENTS

| | | | |
|---|---|---|---|
| CA | 2 514 163 A1 | 8/2004 |
| EP | 0 367 220 A | 5/1990 |
| EP | 0 696 595 A1 | 2/1995 |
| EP | 0252392 B1 * | 11/1995 |
| EP | 0 787 498 A | 8/1997 |
| WO | WO 2004/047859 A2 | 6/2004 |
| WO | WO 2004 071524 A | 8/2004 |
| WO | WO 2006 066595 A | 6/2006 |
| WO | WO 2006/120226 A | 11/2006 |

OTHER PUBLICATIONS

EP Search Report issued in corresp EP 08 38 0312 on Apr. 29, 2009.
Shrake A., et al., "Thermal Stability of Human Albumin Measured by Differential Scanning Calorimetry. I. Effects of Caprylate and N-acetyltryptophanate" *Vox Sanguinis* (1984), vol. 47, No. 1, pp. 7-18.
Mitzner S.R. et al, "Improvement of Hepatorenal Syndrome with Extracorporeal Albumin Dialysis Mars: Results of a Prospective, Randomized, Controlled Clinical Trial" *Liver Transplantation*, Saunders, Philadelphia, PA, US, vol. 6, No. 3, (May 1, 2000) pp. 277-286.
Stegmayr, B.G. "A Survey of Blood Purification Techniques" *Transfusion and Apheresis Science*, Elsevier Science, London, GB, vol. 32, No. 2, (Apr. 1, 2005) pp. 209-220.

* cited by examiner

*Primary Examiner* — Kade Ariani
(74) *Attorney, Agent, or Firm* — Buchanan Ingersoll & Rooney

(57) ABSTRACT

A process for purifying and collecting albumin from plasma and plasma fractions involves diafiltration of an albumin-containing plasma fraction; stabilizing the resulting albumin fraction with sodium chloride and an amino acid in the absence of any added fatty acid; pasteurizing the stabilized albumin fraction; and diafiltering the pasteurized fraction to remove, along other things, stabilizers. In one embodiment, the amino acid stabilizing agent is acetyl tryptophan. The resulting albumin has at least about 80% albumin binding capacity relative to natural plasma albumin, and is storage stable for about 30 months at 30° C.

18 Claims, 4 Drawing Sheets

Comparison of Albumin Binding capacity as a function of the stabiliser and its concentration Comparison of the binding capacity of various albumins Stability of 20 % albumin binding capacity Binding capacity of the albumin of the invention, stabilised with 0.15 M sodium chloride

PROCESS FOR OBTAINING HIGH EFFICIENCY HUMAN ALBUMIN FOR USE IN DETOXIFICATION THERAPY

PRIORITY

This application claims priority to ES200702983, filed Nov. 12, 2007.

DESCRIPTION

The present invention relates to a process for obtaining human albumin with a high capacity for transporting molecules, for use, amongst other applications, for example, in detoxification therapy or cell cultures. The invention is based on experiments carried out to purify human albumin with a high binding capacity for transporting molecules and thereby to increase the efficiency of the detoxification therapy by eliminating toxins in the blood, preferably by albumin infusion methods, plasmapheresis and replacing albumin by an extracorporeal system. The process comprises, according to the invention, a process for obtaining an albumin solution for inactivated therapeutic use of viruses and with a high binding capacity, without stabilising agents or with specific stabilising agents to allow a high binding capacity to be maintained.

BACKGROUND

Quantitatively, albumin is the most important protein in human plasma and plays a fundamental role in the maintenance of the colloidal osmotic pressure of the blood. Albumin also has other properties, such as its antioxidant and anti-free radical activity and also its affinity for union with various endogenous and exogenous substances, such as lipids, fatty acids, bile salts, drugs and toxic substances, amongst other ligands.

The therapeutic use of albumin has been indicated, according to several authors, as a substitution therapy in patients with serious albumin deficiency, hypovolaemic syndrome or shock (serious burns, trauma, or haemorrhages), hypoproteinaemia due to chronic renal diseases and cirrhosis of the liver and also in cases of cardiopulmonary bypass, acute respiratory distress syndrome, haemodialysis and hyperbilirubinaemia. Albumin is also used in the treatment of ascites, acute nephroses, acute nephrotic syndrome, pancreatitis, intra-abdominal infections and acute liver insufficiency.

As the principal transporting molecule in the blood, serum albumin has specific binding sites for lipophilic substances such as fatty acids, bilirubin, etc. The majority of albumin ligands bind to one of the two binding sites I or II. Free fatty acids, metallic ions such as copper and bilirubin bind selectively to specific binding domains.

Normally these substances are transported to the liver by the albumin, where they are degraded. In cases of liver failure these toxic substances stay bound to the albumin saturating its binding capacity, and producing an increase in the levels of toxins in the blood, which accumulate in the tissues and cause general multiorgan failure which can cause the patient's death. In these cases treatment can be carried out by extracorporeal liver support systems which benefit from the binding capacity of commercial therapeutic albumin. Having an albumin with greater binding capacity could be more effective in this type of treatment.

The capacity of albumin to capture and transport a large variety of substances, such as metabolites, metals, toxins, fatty acids, hormones, etc., makes this protein very important.

The processes for obtaining albumin, from human plasma normally start with Fraction V (FrV) of the alcoholic fractionation of plasma according to the Cohn method (Cohn et al., *J Am Chem Soc,* 1946, 68, 459-475). Although this is less frequent, other starting materials can also be used, such as supernatants (S/N) of this Cohn fractionation, such as the S/N of Fraction IV or S/N of Fraction II+III, including an additional stage of purification, such as ion exchange chromatography, for example.

The purification methods that start with these Cohn fractionation intermediaries, with an albumin purity level of >90-95%, are normally based on the separation of polymers, aggregate material and other compounds such as lipoproteins, insolubilised by the effects of the ethanol present in the solution. For an optimum separation of these compounds it is advisable to add albumin of filtration aids (diatomaceous earth) and/or insoluble inorganic silicates (bentonites) or colloidal silica to the suspension. Optionally, according to the type of protein contaminants of the starting material, it can be advisable to add ion exchangers, maintaining conditions which prevent the adsorption of albumin.

Subsequently, elimination of ethanol from the solution is achieved by diafiltration in ultrafiltration equipment, which also allows the elimination of metallic ions and organic carboxylic acid anions such as citrate (Spanish patent P 2.107.390). This ultrafiltration also allows the albumin solution to be brought to the required concentration.

In addition, there is also the possibility of carrying out heat treatment of the solution (preferably heat shock between 56° C. and 63° C.), in order to denaturalise and insolubilise any thermolabile compound remaining in the albumin solution which could destabilise the final product. This heat treatment is also useful in reducing the activity of Prekallikrein Activator (PKA) which is one of the usual contaminants of albumin.

Different methods of albumin purification have been described, which represent variations to that described above, as regards sequencing of stages or adding additional purification stages.

Other methods cover albumin purification by ion exchange chromatography, beginning with fraction V or Supernatant of FrIV, such as U.S. Pat. No. 5,346,992 or EP 0367220. U.S. Pat. No. 4,288,154 suggests a process starting from Supernatant of Fr II+III, also by ion exchange chromatography, with a prior filtration stage in gel.

Human albumin solutions for therapeutic use obtained from plasma by the methods currently known appear in the form of a concentrated solution, generally with 15% to 25% of total protein, are hyperosmotic and cause a movement of fluids from the extravascular to intravascular compartment, or in the form of an isotonic solution of 3.5% to 5% total protein, which is isoosmotic with the plasma. The formulation of these solutions contains albumin, with a purity level of above 95% of total protein, and stabilisers.

When obtaining albumin solutions from human plasma pools, as with other biological products, the risk cannot be excluded of transmitting infection from viruses or other pathogenic agents. Despite this, current therapeutic albumin is considered a safe blood product in the face of this risk. This is especially due to the fact that albumin solutions are pasteurised (heat treatment of at least 10 hours at 60-63° C., generally in the final vial).

From 1941, the date that the first albumin solution from fractionating human plasma was prepared (Cohn et al. *Chem. Rev.,* 1941, 28, 395), studies were begun to stabilise albumin solutions and in 1945 the stabilisation of albumin solution with N-acetyltryptophan, with sodium caprylate or with a mixture of the two was achieved (Scatchard G, et al, *J. Clin.*

*Invest.* 24:671-676, 1945). The stabilisation of albumin solutions continued to be a subject of study (Finlayson J. S. et al, *Vox Sang.* 47:7-18, 1984); (Finlayson J. S. et al, *Vox Sang.* 47:28-40, 1984), but there have been no significant variations until today, this form of stabilisation being accepted by the regulatory authorities of the various countries (for example: European Pharmacopoeia; Human Albumin Solutions monograph 0255). Therefore, at present, commercial preparations of albumin in general contain as stabilisers, caprylate and/or N-acetyltryptophan, in order to avoid polymerisation during the process of pasteurisation and to ensure stability during the storage of the product until its expiry date.

In cases where the therapeutic effect of albumin occurs when capturing toxic compounds as a mechanism prior to its elimination, as in the treatment of hyperbilirrubinaemia, the efficiency of the treatment depends on the albumin having free binding sites.

In studies with models of hyperbilirrubinaemia in neonates, Ebbesen F. (*Acta Pediatr. Scand.* 71:85-90, 1982) establishes that N-acetyltryptophan powerfully displaces bilirubin, so reducing the efficiency of albumin stabilised with N-acetyltryptophan and Caprylate in contrast with albumin stabilised with Caprylate alone. Despite either of the two preparations being effective in protection against encephalopathy caused by bilirubin, the data seem to indicate that stabilisation with N-acetyltryptophan would not be suitable for treatment of hyperbilirrubinaemia, demonstrating the advantage of the stabilisation of albumin with Caprylate.

In other studies, also on the subject of the affinity and capacity of albumin to bind to various compounds, including Tryptophan and Caprylate, it has been established that there is competition between the various compounds for the albumin binding sites (Kragh-Hansen U. *Biochem. J.* (1991) 273, 641-644) and it is accepted that whilst Tryptophan binds to the albumin molecule at a specific site, Caprylate (octanoate) binds to the albumin molecule at various sites, causing a reduction in the capacity of albumin to bind to other compounds.

What is at present beyond all doubt is that these stabilisers bind, at least, to the albumin binding site II and so hinder the transporting function of pasteurised albumin, and can inhibit, at least partly, binding of the endogenous ligands (toxins, etc.) after the intravenous infusion of this albumin.

Attempts have been made in this direction to develop albumin production methods which avoid the use of N-acetyltryptophan and/or sodium Caprylate both during the purification process and in the final composition.

Patent WO2004071524 relates to an albumin preparation process which avoids the inclusion of stabilisers of the N-acetyltryptophan and Caprylate groups. For this we opt for a virus inactivation stage by treatment with Solvent-Detergent (SD) to replace pasteurisation. Treatment with SD has demonstrated great efficiency in virus inactivation with a lipid envelope, but it has no significant effect on the elimination of viruses without an envelope. Another disadvantage of this method is the need to eliminate SD inactivation reagents, which involves the inclusion of extraction stages which complicate, extend and make the process more expensive. Finally, as we have seen, the presence of PKA in albumin solutions is partly reduced by heating. As this patent does not cover heat treatment, it must also include a specific stage for the elimination of this, complicating this process even more.

U.S. Pat. No. 5,919,907 also concerns an attempt to obtain albumin with a greater binding capacity, by developing a process which avoids pasteurisation and thereby adding stabilisers of the N-acetyltryptophan and Caprylate groups. This process takes advantage of the biocide capacity of iodine compounds. Due to the affinity of albumin molecules for iodine and thus the capacity of albumin to neutralise its biocide effect, this method requires, according to said patent, the addition of an iodine compound in a sufficient amount to saturate the binding capacity of albumin and also allow sufficient free iodine to remain in the solution with biocide effect. In this respect, the reproducibility of the process does not seem easy to achieve, this aspect being fundamental to a stage of elimination of pathogens. Moreover, this method requires the elimination of the inactivation reagent, which also involves the inclusion of extraction stages which complicate, extend and make the process more expensive. Another aspect to be considered, not mentioned in said patent, is the presence of PKA in the albumin solutions. As in the previous case, when heat treatment is not performed, a specific stage must be included for the elimination of PKA, which complicates the process.

DESCRIPTION OF THE INVENTION

By means of the investigations carried out, the inventors have established that the binding between Sodium Caprylate and albumin molecules is difficult to reverse, which results in a smaller capacity for binding of toxins by albumin stabilised with caprylate. In addition, the investigators have established that the binding between N-acetyltryptophan and albumin (for therapeutic use, prepared according to the Cohn method and its modifications) is more easily reversible. The possibility of stabilisation with N-acetyltryptophan and without caprylate allows a process to be performed to obtain albumin which includes a stage of virus inactivation by pasteurisation, so that the albumin stabilises in the presence of at least one amino acid and sodium chloride, but without the addition of fatty acids. Surprisingly, the implementation of a purification process for this pasteurised albumin which includes an exhaustive dialysis (diafiltration) process results in a greater binding capacity for the pasteurised albumin.

According to the process described in this invention it is possible to perform the stage of virus inactivation by pasteurisation as an intermediate phase of the process. In this way we can maintain the excellent safety level demonstrated by the therapeutic albumins known to date as regards the possible risk of transmission of pathogens and achieve a reduction in the PKA.

By the method developed in the present invention, it is also possible to obtain albumin with a superior binding capacity including the binding capacity of normal albumin present in plasma, since the process developed allows the reduction of compounds (essentially lipids and fatty acids) closely associated with albumin in its natural state which cause a reduction in its binding capacity, and thereby less efficiency as capturer and transporter of substances, for example in cell cultures and detoxification therapy. The process also allows the reduction of stabilisers added when pasteurisation is performed in an intermediate phase of the process. The albumin so prepared has a very high capacity to bind and transport molecules and allied compounds.

For the preparation of this high binding capacity albumin we can start with a partially purified albumin concentrate, for example in paste (as precipitate). A starting material for this albumin can be Fraction V or Fraction VR (reprecipitate) obtained by alcoholic fractionation by the Cohn method (or versions of it), or by other fractionation process which allow albumin of equivalent purity, typically $\geq$95% of albumin, to be obtained.

Other sources of albumin can be obtained from alcoholic supernatants (S/N) of this Cohn fractionation, for example S/N of Fraction IV, or from S/N of Fraction IV(1)+IV(4), or from Fraction IV(4), or from other supernatants (S/N of Fraction IV(1) or S/N of Fraction II+III) to which an additional stage of purification, for example chromatography, has been included, in order to reach the degree of purification required ($\geqq$95% of albumin).

The albumin thus purified is solubilised in an aqueous medium to a concentration of more than 1%, and typically to 8±2% (p/p), the resulting pH being typically 4.7±0.5, and thus close to the isoelectric point of albumin itself.

If the albumin originates from Fraction V or a supernatant of the Cohn fractionation, the residual ethanol content is normally $\geqq$6%. Otherwise ethanol is added up to the minimum concentration of 6% indicated. During the addition of ethanol or in the solubilisation of the starting material, the suspension cools to a temperature of between −3° C. and 10° C. and is maintained within this temperature range to prevent the denaturalising effects of the hydroalcoholic medium.

Under these conditions insolubilised compounds are left to precipitate, filtration aids (diatomaceous earth) and/or insoluble inorganic silicates (bentonites) or colloidal silica being added to the albumin suspension. Optionally, depending on the type of protein contaminants of the starting material, it is advisable to add inorganic ion exchangers of the perlite type, or even synthetics with amino/ammonium (DEAE, QAE) functional groups, for example DEAE-Sephadex, the pH remaining between 4.2-5.2 in order to prevent the adsorption of the albumin itself. In the absence of ion exchangers the pH of the suspension can then be brought up from 4.2 to 7.5, and preferably be adjusted to pH 6.8-7.2.

Suspension by deep filtration, using filters with mesh which allows the retention of particles sized $\geqq$0.2 μm is explained below. The filtrate is an albumin solution essentially free of insoluble residues of denaturalised protein and other compounds (basically lipoprotein) insolubilised by ethanol.

The product obtained is subjected to diafiltration by polyethersulphone membranes or equivalents, whose nominal molecular cut-off is between 1 and 50 kDa and preferably between 10 and 30 kDa. Diafiltration with water for injection or preferably with a saline solution of $\geqq$0.15 M concentration of NaCl can be achieved under the same conditions of pH 4.2 to 7.5 which are found in the filtrate originating from the previous stage, but preferably, and depending on the presence of lipids, a choice will be made to adjust to pH 4.2-5.2. In addition, the saline concentration also promotes the dissociation of metallic ions such as aluminium or iron and anions of more strongly associated organic carboxylic acids, such as citrate.

In accordance with the conventional technique of ultrafiltration we proceed to the first phase of concentration, reaching approximately between 8-15% of protein and then diafiltration is performed by adding solvent at a constant volume. The amount of diafiltration solution must not be less than 3 volumes, and preferably more than 7 volumes.

The albumin solution adjusted to a pH close to neutral can be stabilised by adding NaCl to a concentration of $\geqq$0.15 M and at least one amino acid, preferably using an amount of $\geqq$0.096 mmol of N-acetyltryptophan/g of albumin. This stabilised solution can be sterilised by absolute filtration through 0.2 μm pore size, collecting in bulk as intermediate material and continuing with its pasteurisation in this phase.

Inactivation of viruses by pasteurisation has the advantage of being effective independently of whether the viruses have a lipid coating or not, this being a clear advantage for chemical treatments, with SD for example.

The intermediate heat treated bulk solution is clarified by filtration and submitted to exhaustive diafiltration in order to reduce the stabilisers added during the previous stage.

The second diafiltration stage is carried out under the same conditions of application as in the initial phase before heat treatment, allowing for the final albumin solution to reach isotonia (approximately 0.15 M NaCl), and the protein concentration is adjusted to the desired value, between 3.5% and 25%, approximately.

Given that N-acetyltryptophan used as stabiliser is extensively eliminated in the form indicated by diafiltration, the number of applied volumes of diafiltration solution is established as a function of the amount of the remaining stabiliser.

Optionally, it is possible to add a stage of virus elimination by nanofiltration to the process. Virus elimination by nanofiltration, like pasteurisation, is also effective independently of whether or not coated viruses are concerned. The efficiency of nanofiltration is a function of the pore size of the nanofilter used, depending on the solution to be filtered. In the case of albumin solutions nanofiltration is possible with pore sizes of 15 nm, with which significant reductions in viruses considered to be the smallest can be guaranteed. The incorporation of a nanofiltration stage with pores of very small size as a complement to pasteurisation does not require the presence of stabilisers, as the binding capacity of the albumin obtained is not affected thereby. In addition the combination of pasteurisation and nanofiltration increases the product's safety level, if a higher level is appropriate.

To achieve nanofiltration of albumin to make it really effective in relation to the set of viruses transmissible by the blood, including the most minute, it is required that the content of compounds be of high molecular weight or the aggregates present in the product to be very discrete, so it is advisable to implement this stage at a point prior to the heat treatment.

At this time the use of commercial nanofilters of a different filtration pore size has been described, which the retentive efficiency with regard to viruses varies according to the pore size selected. For the application of albumin, 50 nm, 35 nm, 20 nm and 15 nm filters can be used, which can also be coupled in series of two or more, forming a decreasing gradient of pore sizes. It is also possible to achieve double nanofiltration with the same pore size, which increases the retention of possible pathogens.

The conditions for the concentration of protein vary according to the nanofilter pore size. Therefore, for sizes smaller than 15 and 20 nm it is advisable to thoroughly dilute the albumin to concentrations of less than 5%, and preferably between 0.5-2%. However, when the pore sizes are between 35 and of 50 nm or more, direct nanofiltration at concentrations of $\geqq$5% of albumin is feasible. Ambient temperature (18-25° C.) and approximately neutral pH conditions are the most suitable to facilitate filtration.

In any case concentration by ultrafiltration after nanofiltration can be necessary to adjust to the final formulation desired.

An acceptable form of conservation of high efficiency albumin of the invention is freeze-drying, for which the use of stabilisers is not required.

For conservation of albumin in solution its stabilisation may be necessary, and this can be effected with $\geqq$0.15 M sodium chloride. Albumin stabilised in this form has a correct level of stability if it is kept cold (between 2 and 8° C.).

Another form of stabilisation would be performed with sodium chloride $\geqq$0.15 M and N-acetyltryptophanate, at a concentration of $\geqq$0.096 mmol/gram of albumin, preferably 0.16 mmol/gram of albumin. The solution stabilised with this formulation has correct level of stability for being kept for at least 30 months in liquid at a temperature of less than or up to 30° C., or for a shorter time but at a higher temperature. In any case the incorporation of fatty acids must be avoided.

To determine the albumin binding capacity (ABiC) a method based on the change in fluorescence occurring when binding a specific fluorimetric marker, such as dansylsarcosin, to the binding II site of the albumin is used. After diluting the various albumin samples to the same concentration and incubating them with the marker, the marker molecules not bound are separated by filtration, by assessing the amount of free dansylsarcosin by fluorimetric detection (λ excitation=355 nm and λ emission=460 nm). The binding capacity is quantified as follows:

$$\% \; ABiC = \frac{\text{reference albumin } RFU - \text{reference white albumin } RFU}{\text{sample } RFU - \text{white } RFU \text{ of sample}} \cdot 100$$

(RFU: Relative fluorescence units)

Having determined the binding capacity by this method and taking as reference the binding capacity of natural human plasma albumin (100%), we consider that a high binding capacity is within at least 80% of the binding capacity of natural human plasma albumin.

For the purposes of the present invention, high albumin binding capacity is defined as an ABiC value in % greater than that of commercial albumins stabilised with sodium caprylate or with a mixture of sodium caprylate and N-acetyltryptophan.

Specifically the present invention consists of a process to obtain a pasteurised albumin solution, with a high molecule binding capacity including the following stages:
a) a first dialysis (diafiltration)
b) stabilising the solution with NaCl and at least one amino acid
c) heating the solution
d) a second dialysis (diafiltration)

This process is applicable to any albumin solution independently of its origin, either originating from human plasma, or obtained by recombinant or transgenic methods.

The process for obtaining albumin solution with a high binding capacity for molecules includes heating the albumin solution (pasteurisation), in order to inactivate viruses and reduce the PKA content. This heating process is performed at a temperature of 61±2° C. for 10.5±0.5 hours.

In order to allow the albumin solution to be heated, it is stabilised with sodium chloride (NaCl) at a concentration of or greater than 0.15 M and the addition of at least one amino acid. This amino acid is preferably N-acetyltryptophan in an amount of or greater than 0.096 mmol of N-acetyltryptophan/g of albumin.

This process is distinguished specifically by not adding fatty acids to the albumin solution.

The process described for obtaining an albumin solution with a high binding capacity for molecules, includes the elimination by diafiltration of substances linked to albumin, which reduce its binding capacity. These substances linked to albumin can be natural ligands, already bound to the albumin before its purification, or substances added (stabilisers) during the purification process.

The elimination by diafiltration of substances linked to the albumin is carried out in two stages. The first stage of diafiltration is performed before stabilisation in order to heat the solution. The second stage of diafiltration is performed after heating the solution (pasteurisation). In the second stage of diafiltration the amino acid added as a stabiliser is eliminated.

In the process described for obtaining albumin solution with a high binding capacity for molecules, the stages of diafiltration are carried out on no less than 3 volumes of NaCl solution and preferably on 7 volumes. Following diafiltration of a solution of NaCl, it is diafiltered in water to adjust the concentration of salts of the solution to the desired value.

The present invention is described in more detail with reference to the following examples, to which, however, it is not to be considered limited.

Example 1

Comparison of the Effect on the Albumin Binding Capacity (ABiC) by N-acetyltryptophan and Sodium Caprylate Stabilisers In order to achieve albumin with a high binding capacity, it was decided to assess to what extent sodium caprylate and N-acetyltryptophan stabilisers, normally used for stabilising commercial preparations, affected an albumin binding capacity without stabilising.

For this the ABiC was determined in accordance with the established method, but taking as reference an albumin without stabilisers. Separate solutions of each excipient (N-acetyltryptophan and caprylate) were prepared in increasing concentrations. 1 ml of each solution was incubated with 1 ml of albumin without stabilisers (final albumin concentration 1%). Then 1 ml of dansylsarcosin was added to each mixture and the normal process was followed using the albumin binding capacity quantification method.

Figure 1:
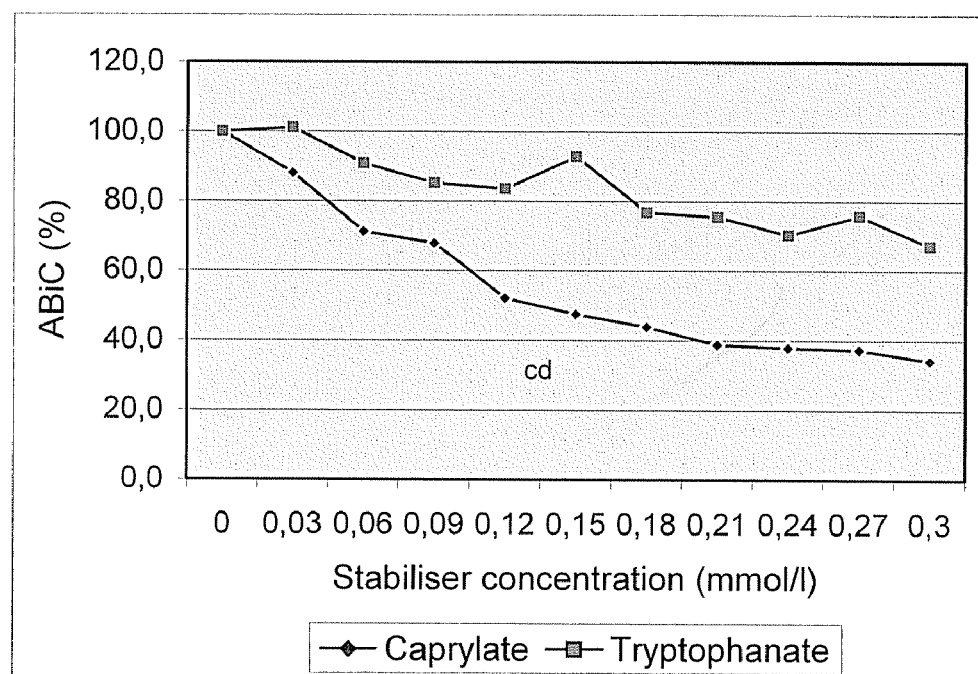
FIG. 1 discloses a comparison of albumin binding capacity as a function of the stabilizer and its concentration.
Figure 2:
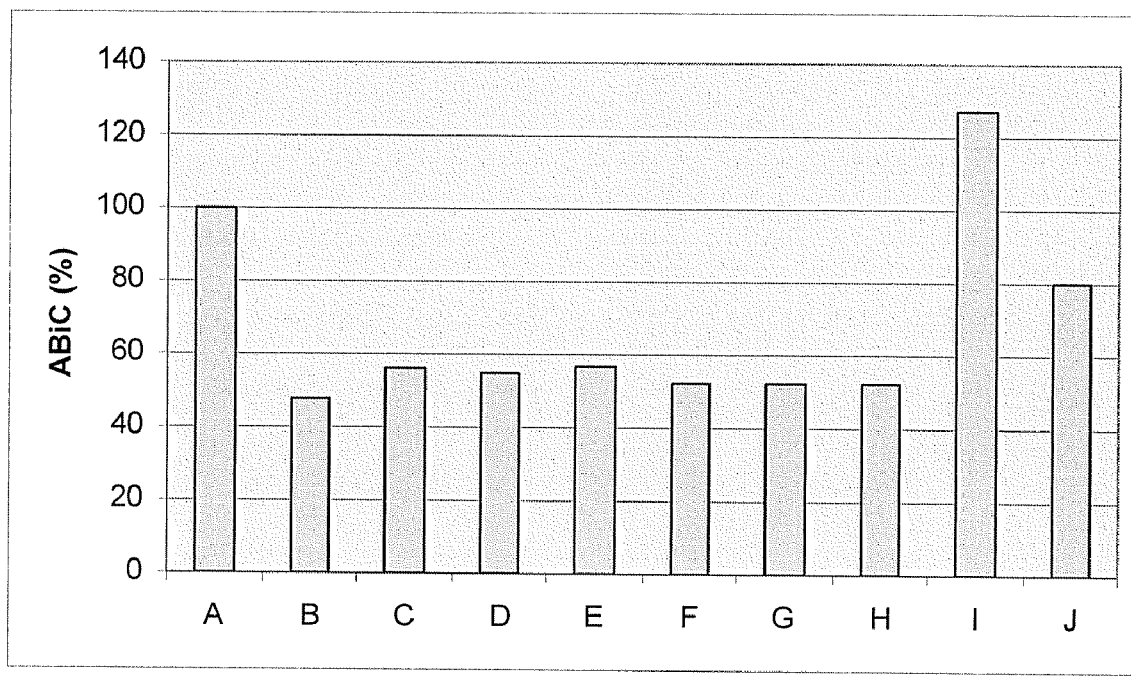
FIG. 2 discloses a comparison of the binding capacity of various albumins.

The results obtained (FIG. 1) show, for the same concentration of excipients, that the albumin binding capacity is lower when caprylate is added than when N-acetyltryptophan is added. These results support a greater affinity to albumin of caprylate than of N-acetyltryptophan.

Example 2

Comparison of Plasma Albumin Binding Capacity (ABiC) with Various Commercial Albumin Concentrates and with Albumin Prepared According to Method Described in the Present Invention, without Stabilisers and Stabilised with N-Acetyltryptophan at 0.16 mmol/g Taking the binding capacity shown by natural plasma albumin (100%) (column A) as a reference albumin, we observe that in different commercial concentrates of albumin, with a concentration of stabilisers, N-acetyltryptophan and sodium caprylate of between 0.064 and 0.096 mmol/g albumin, the binding capacity is of the same order in all (48% to 57%) (columns B to G) and of the same order as the binding capacity of a commercial albumin stabilised only with sodium caprylate (0.099 mmol/g albumin) (52%) (column H). This binding capacity is less than that of plasma albumin.

The greater binding capacity of albumin obtained according to the present invention, without stabilisers, (127%) (column I) or that stabilised with N-acetyltryptophan at 0.16 mmol/g (80%) (column J) upon comparing it with commercial concentrates of albumin, is also observed.

These results indicate, on the one hand, the advantage of the purification method described for obtaining albumin with a superior binding capacity, and on the other the considerable interference to the binding albumin capacity caused by the stabilisers analysed, sodium caprylate and N-acetyltryptophan.

Example 3

Stability of albumin solution. An albumin solution, at a concentration of 20%, obtained by the process described in the present invention is stabilised with 0.15 M sodium chloride and N-acetyltryptophanate at a concentration of 0.16 mmol/gram of albumin and a study is made of its stability in accordance with the current regulations for stability studies, harmonised at international level, Q5C "Stability testing of Biotechnological/Biological products" and Q1A(R2) "Stability testing of new drugs, substances and products"

Figure 3:
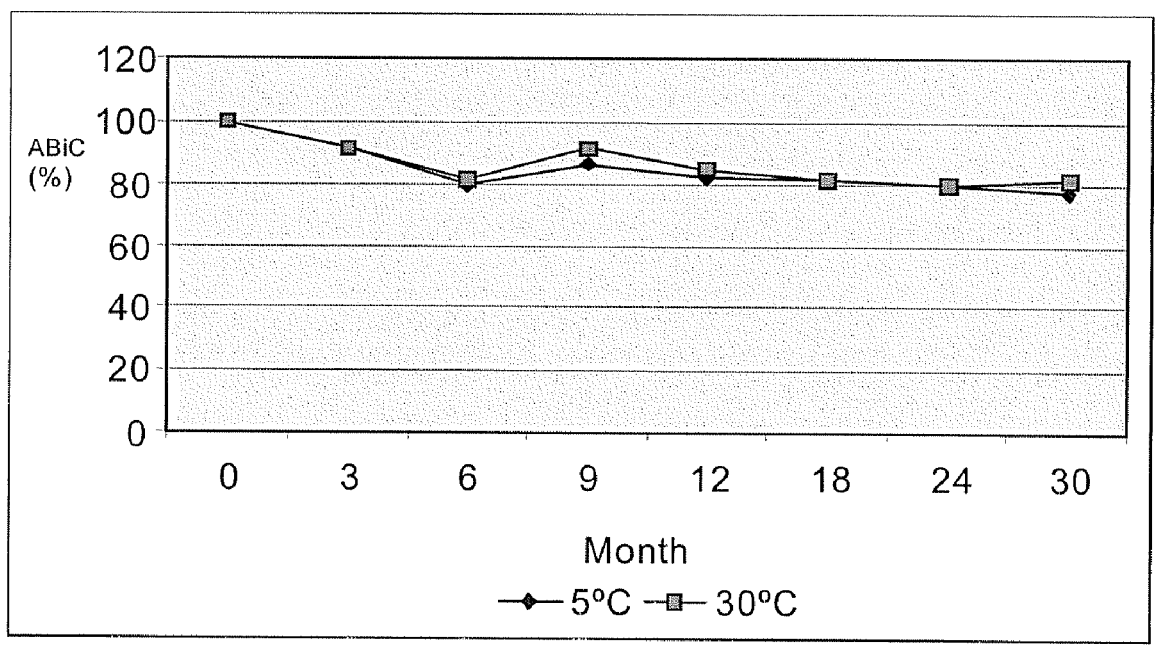
FIG. 3 discloses the stability of an albumin solution, at a concentration of 20%, according to its binding capacity.

Stability data in real time of 3 batches of the albumin indicated show that the product is kept stable. Specifically, the binding capacity does not show considerable variations with respect to the start of the study, at least after 30 months of storage at 5° C.±3° C. and at 30° C.±2° C. (FIG. 3). In fact oscillations observed in the binding capacity results over time occur in parallel at 5° C. and at 30° C., and are therefore attributable to the actual variability of the test, performed on different days, rather than a true variation in this binding capacity.

Example 4

Figure 4:
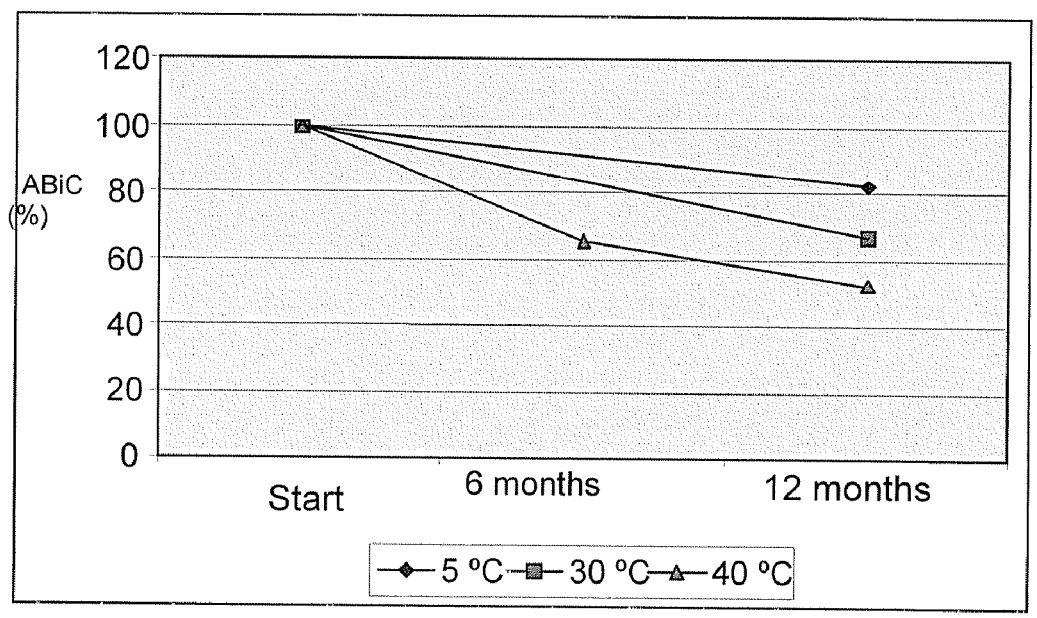
FIG. 4 discloses the binding capacity of high efficiency human albumin, stabilised with 0.15M sodium chloride.

Stability of an Albumin Solution Obtained by the Process Described in the Present Invention and Stabilised with 0.15 M Sodium Chloride The real time stability data of the albumin indicated, at storage temperatures of 5° C., 30° C. and 40° C. show that the product is kept stable at a temperature of 5° C. At this temperature, the binding capacity (FIG. 4) shows no large variations with respect to the start of the study nor compared with the albumin stabilised with N-Acetyltryptophan. The molecular distribution and turbidity data (Table 1) also support the stability of this albumin solution.

TABLE 1

Stability of the albumin of the invention
stabilised with 0.15 M sodium chloride

| MOLECULAR | MONTHS | |
|---|---|---|
| DISTRIBUTION: | 0 | 12 |
| Polymer (%) | 0 | 0 |
| Dimer (%) | 5.6 | 3.6 |
| Monomer (%) | 94.4 | 95.1 |
| Fractions (%) | 0 | 1.3 |
| TURBIDITY (NTU) | 5.0 | 5.3 |

The process of the invention is illustrated in the following diagram

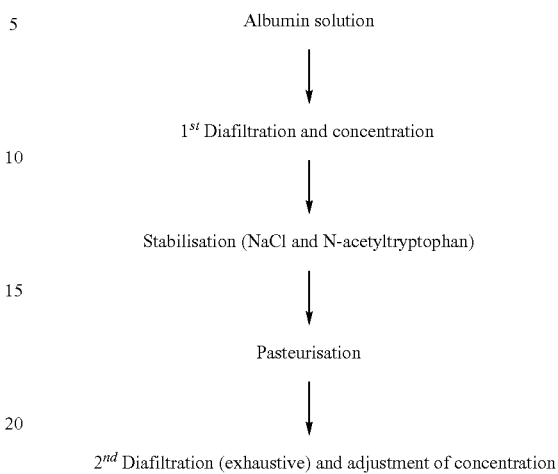

As can be appreciated from the foregoing, the inventors have demonstrated the great advantage of the use of human albumin with a high binding capacity for detoxification therapy by means of investigations performed with regard to the stabilisation of albumin and elimination of the stabilisers associated therewith and their effect on the capacity for union of albumin.

Human albumin used in detoxification therapy is distinguished by the fact that its final formulation totally lacks stabilisers or rather includes stabilising agents which result in a high binding capacity.

The detoxification therapy can be performed by infusion of albumin to the patient, by plasmapheresis and replacement of albumin in the patient or also be performed in an extracorporeal system.

Although the present invention has been explained in the previous description in accordance with the examples shown, the latter are not intended to limit its scope, therefore it should be considered that all the variants which are included in the following claims are within the scope of the present invention.

The invention should not be considered as limited by the above description; rather the scope and limitations of the invention are defined by the enclosed claims, and equivalents thereof.

The invention claimed is:

1. A process for obtaining albumin from plasma comprising:
   a) diafiltration of an albumin-containing plasma fraction;
   b) stabilizing the diafiltered albumin fraction with NaCl and one or more amino acids and in the absence of any added fatty acids;
   c) pasteurizing the stabilized albumin fraction; and
   d) diafiltration of the pasteurized albumin fraction,
   wherein the resulting albumin has albumin binding capacity of at least about 80% relative to natural human plasma albumin.

2. The process of claim 1, wherein the plasma fraction is human plasma.

3. The process of claim 1, wherein the pasteurizing of step (c) is effected at a temperature and duration sufficient to inactivate viruses and reduce PKA content.

4. The process of claim 3, wherein the pasteurizing is performed by heating the stabilized albumin fraction to 61±2° C.

5. The process of claim 4, wherein the stabilized albumin fraction is heated for 10.5±0.5 hours.

6. The process of claim 1, wherein the albumin is stabilized by adjusting the fraction to at least 0.15 M NaCl.

7. The process of claim 6, wherein the amino acid is N-acetyltryptophan.

8. The process of claim 7, wherein the albumin is stabilized by adjusting the fraction to at least 0.096 mmol of N-acetyltryptophan/gram albumin.

9. The process of claim 1, wherein the diafiltration of step (d) is carried out such that it removes substances binding to albumin that reduce the its binding capacity of albumin.

10. The process of claim 1, wherein the diafiltration of step (d) is carried out to achieve an albumin fraction that is about 0.15 M NaCl and a protein concentration of about 3.5 to 25%.

11. The process of claim 1, further comprising sterilization of the stabilized albumin fraction by passing it through a filter of pore size 0.2 μm.

12. The process of claim 1, wherein diafiltration is performed using a membrane having a nominal molecular cutoff of 1-50 kDa.

13. The process of claim 1, wherein the resulting albumin retains at least about 80% albumin binding capacity on storage for 30 months at 30° C.±2° C.

14. The process of claim 1, wherein the diafiltration of step (d) removes added amino acid of step (b).

15. The process of claim 1, wherein a diafiltration step is performed on a NaCl solution.

16. The process of claim 15, wherein a diafiltration step is performed on no less than 3 volumes of NaCl solution.

17. The process of claim 15, wherein a diafiltration step is performed on no less than 7 volumes of NaCl solution.

18. The process of claim 15, wherein a diafiltration step on a NaCl solution is followed by diafiltration on water.

* * * * *